United States Patent [19]

Yost et al.

[11] Patent Number: 5,325,339

[45] Date of Patent: Jun. 28, 1994

[54] ABSOLUTE CALIBRATION TECHNIQUE FOR BROADBAND ULTRASONIC TRANSDUCERS

[75] Inventors: William T. Yost, Newport News; John H. Cantrell, Tabb, both of Va.

[73] Assignee: The United States of America as represented by the Administrator of the National Aeronautics and Space Administration, Washington, D.C.

[21] Appl. No.: 117,511

[22] Filed: Aug. 31, 1993

[51] Int. Cl.$^5$ .................... H04B 17/00; G01D 18/00
[52] U.S. Cl. .................................................. 367/13
[58] Field of Search .................... 367/13, 140, 181; 73/1 DV

[56] References Cited

U.S. PATENT DOCUMENTS

| | | | |
|---|---|---|---|
| 4,310,906 | 1/1982 | Cantrell, Jr. et al. | 367/181 |
| 4,434,648 | 3/1984 | Drost et al. | 367/13 |
| 4,445,361 | 5/1984 | Moffett et al. | 73/1 DV |
| 4,942,614 | 7/1990 | Hamilton | 367/13 |

OTHER PUBLICATIONS

Yost et al., Absolute Ultrasonic Displacement Amplitude Measurements with a Submersible Electrostatic Acoustic Transducer, Review of Scientific Instruments, vol. 63, No. 9, pp. 4182–4188, Sep., 1992.

Primary Examiner—Ian J. Lobo
Attorney, Agent, or Firm—Kimberly A. Chasteen

[57] ABSTRACT

Calibrating an ultrasonic transducer can be performed with a reduced number of calculations and testing. A wide-band pulser is connected to an ultrasonic transducer under test to generate ultrasonic waves in a liquid. A single frequency is transmitted to the electrostatic acoustic transducer (ESAT) and the voltage change produced is monitored. Then a broadband ultrasonic pulse is generated by the ultrasonic transducer and received by the ESAT. The output of the ESAT is amplified and input to a digitized oscilloscope for Fast Fourier Transform. The resulting plot is normalized with the monitored signal from the single frequency pulse. The plot is then corrected for characteristics of the membrane and diffraction effects. The transfer function of the final plot is determined. The transfer function gives the final sensitivity of the ultrasonic transducer as a function of frequency. The advantage of the system is the speed of calibrating the transducer by a reduced number of measurements and removal of the membrane and diffraction effects.

31 Claims, 3 Drawing Sheets

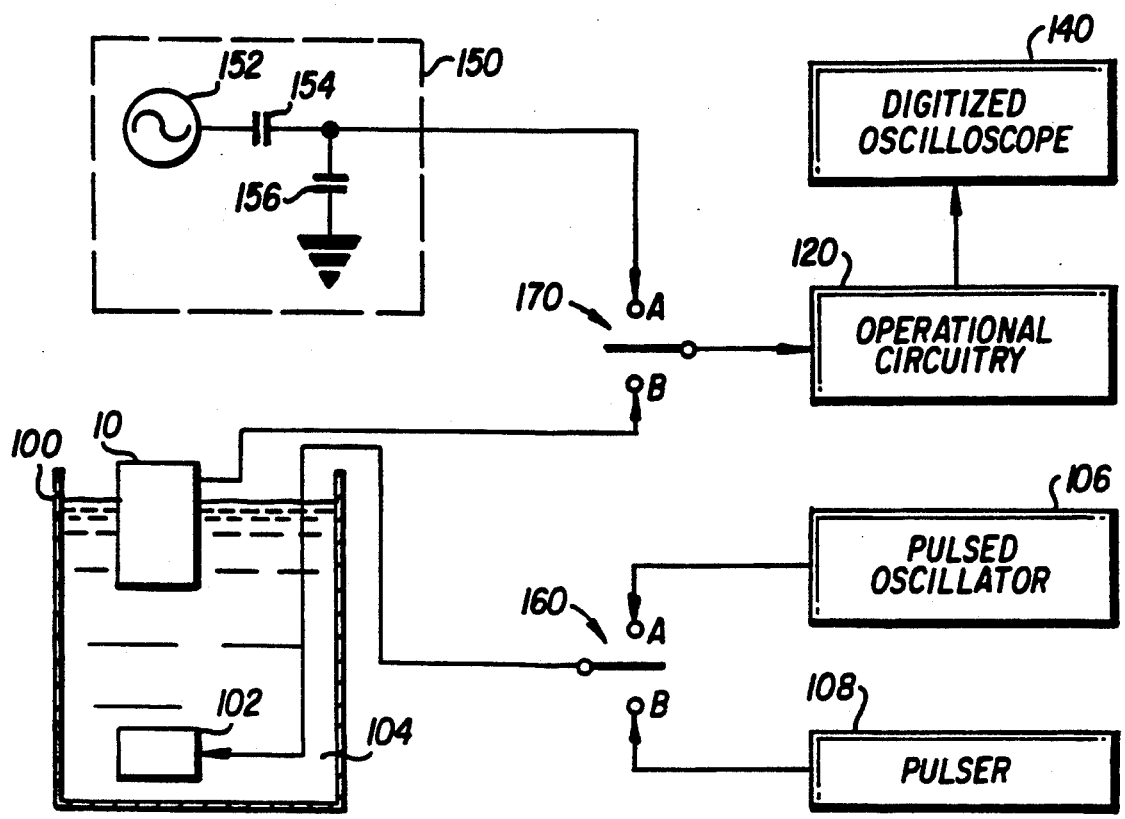
FIG. 3
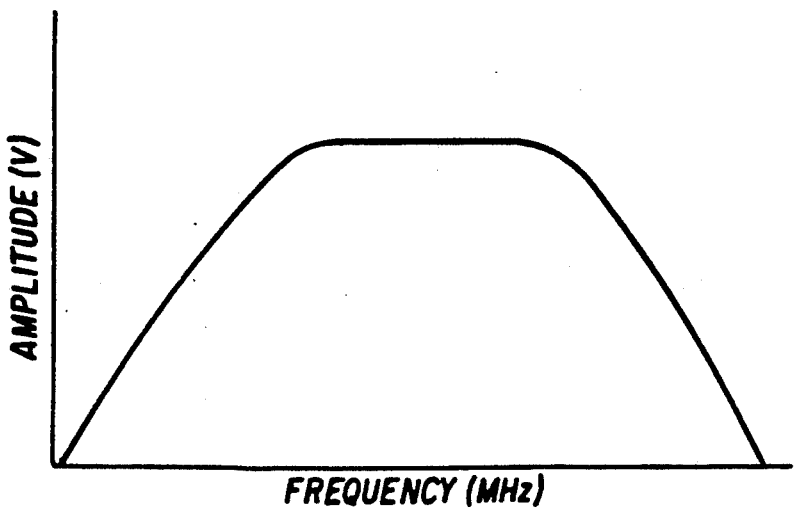
FIG. 5   FOURIER TRANSFORM OF ESAT OUTPUT

ABSOLUTE CALIBRATION TECHNIQUE FOR BROADBAND ULTRASONIC TRANSDUCERS

ORIGIN OF THE INVENTION

The invention described herein was made by employees of the U.S. Government and may be manufactured and used by or for the Government for governmental purposes without the payment of any royalties thereon or therefor.

BACKGROUND OF THE INVENTION

1. Field of the Invention

This invention relates to improvements in the calibration of broadband ultrasonic transducers. More particularly, this invention calibrates a broadband ultrasonic transducer without using another device as the standard and reduces the number of measurements required to calibrate the transducer.

2. Description of the Related Art

Broadband capacitive electrostatic acoustic transducers are used for absolute amplitude ultrasonic measurements in liquid environments. These transducers are air-tight enclosures with a conductive membrane as part of its outside surface. A central electrode that has a flat end is mounted inside the enclosure so that the flat end is approximately parallel to the conductive membrane. This forms a capacitor.

The frequency response of the electrostatic acoustic transducer (ESAT) has a frequency range from sub-MHz to above 15 MHz depending on the membrane. These ESATs can also be used to measure the absolute amplitudes of ultrasonic compressional waves in liquids. These measurement techniques make the ESAT especially useful in the study of ultrasonic properties of liquids, including liquid-state anharmonicity, ultrasonic dosimetry in medical and biological applications, and also ultrasonic spectral analysis.

SUMMARY OF THE INVENTION

The invention calibrates a broadband ultrasonic transducer (UT) by using an ESAT. One preferred embodiment reduces the number of calculations and measurements that must be performed in order to calibrate the UT. A wideband pulser is connected to the UT to be calibrated to produce ultrasonic waves in a liquid in which the ESAT is placed. A single frequency, e.g. a toneburst, is generated and transmitted to the ESAT. The signal resulting from the time-varying change in capacitance produced by the toneburst is measured. Next, a broadband ultrasonic pulse is generated and transmitted to the ESAT. The output of the ESAT is amplified in a digitized oscilloscope and a plot is generated using a Fast Fourier Transform. The plot is normalized using the measured signal resulting from the time-varying change in capacitance due to the toneburst. Then the plot is modified to correct for membrane characteristics and diffraction effects. A transfer function is calculated that gives the final sensitivity of the UT as a function of frequency. The advantage of the system is the speed of the measurement and the removal of the membrane and diffraction effects.

BRIEF DESCRIPTION OF THE DRAWINGS

The invention is illustrated in the accompanying drawings, in which like reference numerals are used to denote like or similar parts, and wherein:

FIG. 3 is a set-up for calibrating an ultrasonic transducer using the method of the invention;

FIG. 5 is a plot of a Fast Fourier Transform; and

DETAILED DESCRIPTION OF PREFERRED EMBODIMENTS

Figure 1:
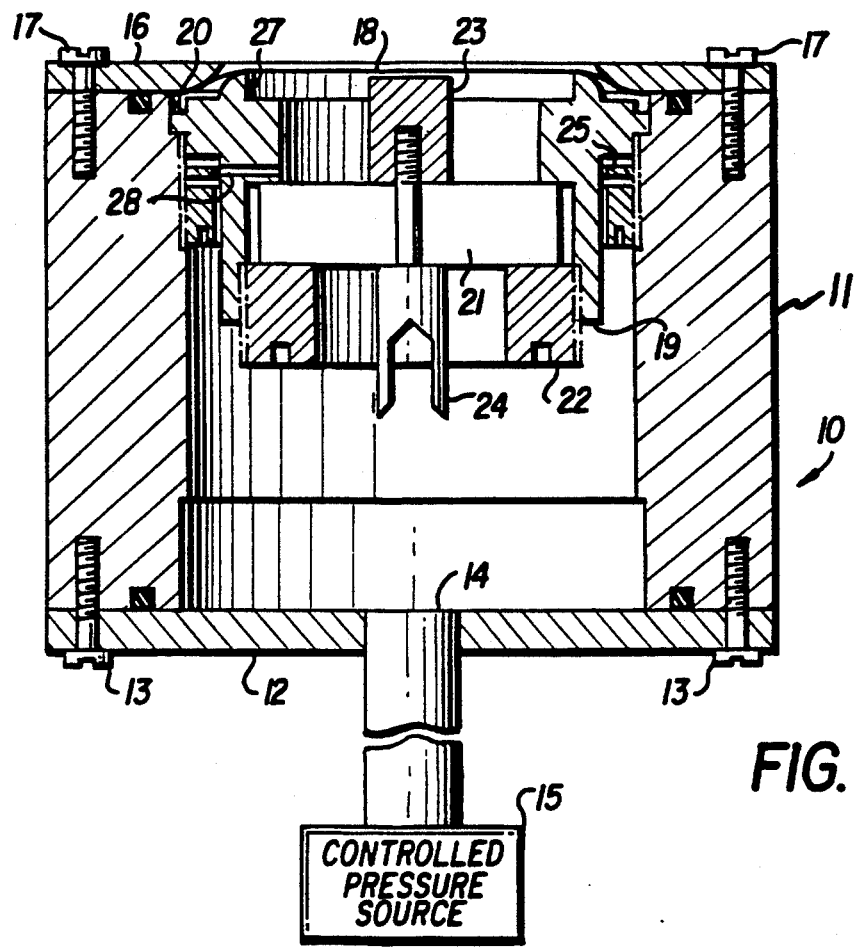
FIG. 1 is a sectional schematic drawing of an electrostatic acoustic transducer (ESAT)

Referring now to the drawings, where the drawings are for the purpose of describing the preferred embodiment of the invention and not for limiting same, the elements of an electrostatic acoustic transducer will be described.

The following is brief description of an electrostatic acoustic transducer disclosed in U.S. Pat. No. 4,310,906, which is incorporated herein by reference. In FIG. 1, an electrostatic acoustic transducer 10 is shown. A cylindrical housing 11 is made from an electrically conductive material, e.g. brass. An electrically conductive plate 12 is attached using screws 13 to one end of the cylindrical housing 11. An opening 14 in the plate 12 is connected to a controlled pressure source 15, which controls the pressure inside the housing. An electrically conductive retainer ring 16 is attached using screws 17 to the other end of the cylindrical housing 11. An electrically conductive membrane 18, which is approximately 11 $\mu$m thick, covers the opening left by the retainer ring 16 in order to complete an air-tight enclosure.

A slide assembly 19, which is located inside housing 11, fits into a slot 20 to allow movement of the slide assembly in the axial direction only. An insulator 21 is mounted on the slide assembly 19 by a holding collar 22. The holding collar 22 is threaded through the slide assembly 19. A cylindrical central electrode 23 is mounted on the insulator 21 by a suitable fitting 24. A washer 25 is fitted inside the housing 11 against the slide assembly 22. A tension ring 26, which is treaded to housing 11, pushes washer 25 and slide assembly 19 upward in the axial direction.

Slide assembly 19 has a protruding annular lip 27, pressed against membrane 18, thereby tensioning the membrane 18 as it is pressed against retainer ring 16. the protruding annular lip 27 provides enough tension on the slide assembly to remove all wrinkles from the membrane 18. Also, the protruding annular lip 27 ensures that the gap between the membrane 18 and the central electrode 23 is approximately 10 $\mu$m. The air pressure in the inside of the ESAT 10, controlled by the controlled pressure source 15, is used to control the spacing between the membrane 18 and the central electrode 23 during operation. A pressure equalization hole 28, which is located in the slide assembly 19, equalizes the pressure between the chamber inside the housing and the membrane 18.

Figure 2:
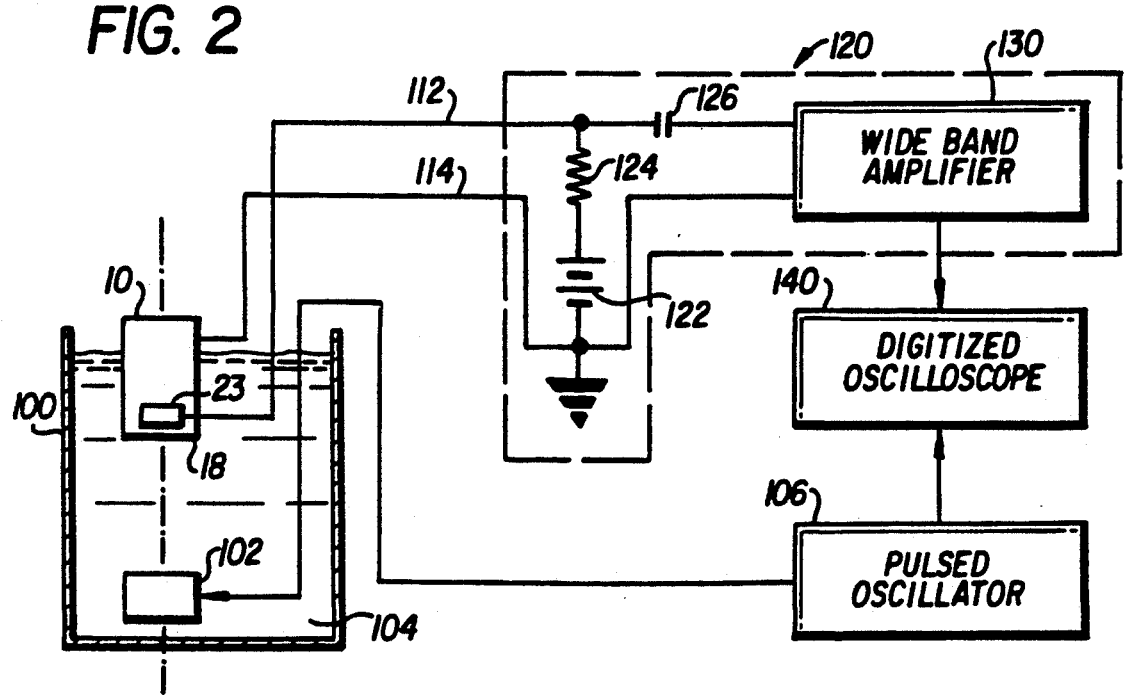
FIG. 2 is a set-up for using an electrostatic acoustic transducer.

The operation of the ultrasonic transducer will be briefly described with reference to FIG. 2. A transducer 102, such as a damped piezoelectric transducer, is emerged in a liquid 104 contained in container 100. A pulsed oscillator 106 supplies pulses to the transducer 102 causing it to emit ultrasonic signals into the liquid 104. The ESAT 10 is also submerged in the liquid 104 and is coaxially located above the transducer 102. The ultrasonic signals emitted by the transducer 102 are detected by the ESAT 10 and measured.

The electrically conductive membrane 18 and the central electrode 23 are shown in the ESAT 10. Leads 112 and 114 are connected to a circuit 120 for monitoring the signal generated as the result of capacitance variations between the membrane 18 and the central electrode 23. The membrane 18 is connected to a ground and also to the DC voltage source 122. The central electrode 23 is connected to a first end of a capacitor 126 and to a first end of a resistance 124, which is connected at its other end to the a lead of the DC voltage source 122. The second end of the capacitor 126 is connected to a wideband amplifier 130. The membrane 18 and the central electrode 23 can be connected in reverse to circuit 120.

Changes in capacitance between central electrode 23 and membrane 18 are converted to changes in voltage. These voltage changes are passed through capacitor 126 to the wideband amplifier 130. The output of the wideband amplifier 130 can be connected to any other circuitry desired. In the preferred embodiment, the wideband amplifier 130 is connected to a digitized oscilloscope 140 for display and analysis. The digitized oscilloscope 140 is triggered by an output of the pulsed oscillator 106. Capacitor 126 passes only voltage changes and hence does not allow DC voltage at source 122 to pass to the wideband amplifier 130. The output of the wideband amplifier 130 can then be analyzed to give an indication of the properties of liquid being analyzed. See the above incorporated U.S. Pat. No. 4,310,906 for further details.

Referring to FIG. 3, the test equipment for standardizing an ESAT is shown. The ESAT 10 to be standardized is immersed in a liquid 104 contained in the container 100. The ultrasonic transducer 102 to be calibrated is located near the bottom of the container 100. The UT 102 is connected to the pulsed oscillator 106 and a pulser 108 via a switch 160. The membrane and the central electrode of the ESAT 10 are connected to the operational circuitry 120 (shown in FIG. 2) via switch 170. The calibration circuitry 150 is also connected to the operational circuitry 120 via switch 170. The output of the operational circuitry 120 is connected to a digitized oscilloscope 140 or other device capable of giving a fourier transform of the input.

The calibration circuitry comprises a calibration generator 152 connected to a first side of a gap capacitor 154. The second side of the gap capacitor 154, which is used as the output, is connected to a second capacitor 156 for filtering the stray capacitance of the ESAT. The second capacitor 156 is connected to ground.

Figure 4:
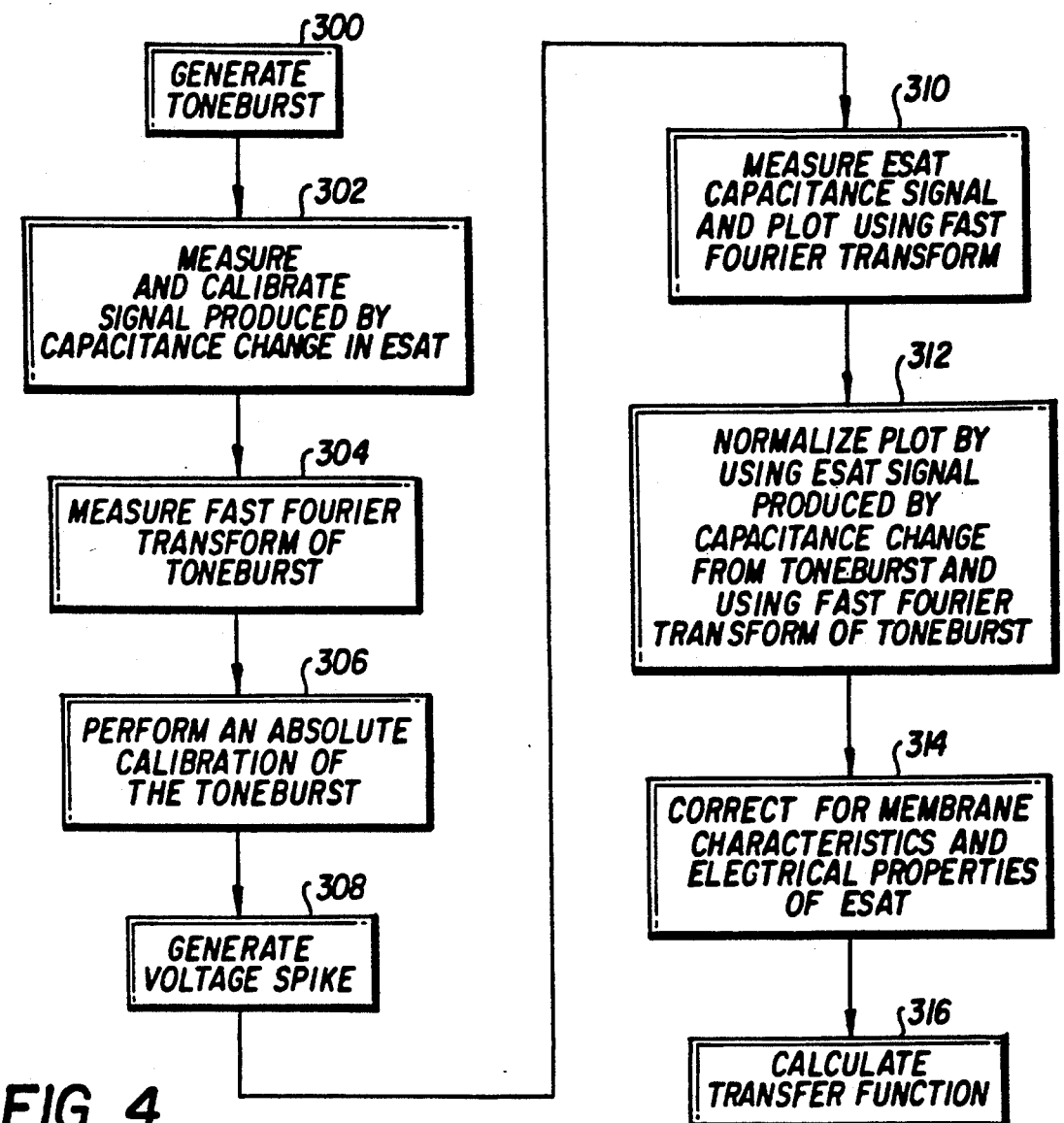
FIG. 4 is a flowchart of a method for standardizing an electrostatic acoustic transducer.

The method of standardizing an ESAT next will be described with reference to FIG. 4. A single frequency ultrasound wave, such as a toneburst, is generated by the ultrasonic transducer 102 to be calibrated in step 300. The pulsed amplifier 106 sends the appropriate signal to the UT 102 to generate such a toneburst. The ESAT 10 receives the single frequency waveform and produces a time-varying change in capacitance between the membrane 18 and the central electrode 23, as described earlier. In step 302, the amplitude of the signal generated by the capacitance change is measured and stored. The Fast Fourier Transform of the toneburst is measured in step 304.

In step 306, an absolute calibration of the toneburst is performed by connecting the calibration circuitry 150 to the operational circuitry 120 via switch 170. The calibration generator 152 is adjusted to match the capacitance change in the ESAT measured in the step 302. The level of the calibration generator 152 is stored.

In step 308, a voltage spike is generated by the UT 102, which is connected to the pulser 108 via switch 160. The voltage spike contains many frequencies, preferably the entire frequency spectrum measurable by the ESAT 10. The ESAT signal output, which results from reception of the ultrasonic wave generated by the UT 102 in response to the voltage spike, is input through the operational circuitry 120 via switch 170 to the digitized oscilloscope 140. The waveform is plotted in step 310 using a Fast Fourier Transform algorithm on the digitized oscilloscope 140. A typical Fast Fourier Transform plot is shown in FIG. 5. The amplitude is plotted as a function of frequency.

In step 312, the ESAT output signal resulting from the capacitance change due to the single frequency toneburst (measured in step 302) is used to normalize the Fast Fourier Transform plot of the voltage spike. The plot is normalized using the ESAT signal produced by capacitance change from the toneburst and the Fast Fourier Transform of the toneburst calculated in step 304.

For example, a 5 MHz toneburst produces an ESAT signal output of 7.5 volts. This output signal corresponds to a sinusoidally time-varying 2 Å movement of the membrane 18 relative to the central electrode 23. Next, the broadband signal output from the ESAT resulting from the voltage spike in the UT 102 is monitored and the Fast Fourier Transform is performed. On the Fast Fourier Transform plot of the voltage spike, a frequency of 5 MHz produces an amplitude of 5 volts. The difference between the actual measured signal at the toneburst frequency and the signal obtained at 5 MHz on the Fast Fourier Transform plot is represented by the ratio:

$$\frac{7.5}{5} = 1.5 \qquad (1)$$

Therefore, the Fast Fourier Transform plot is adjusted by a factor of 1.5.

Figure 6:
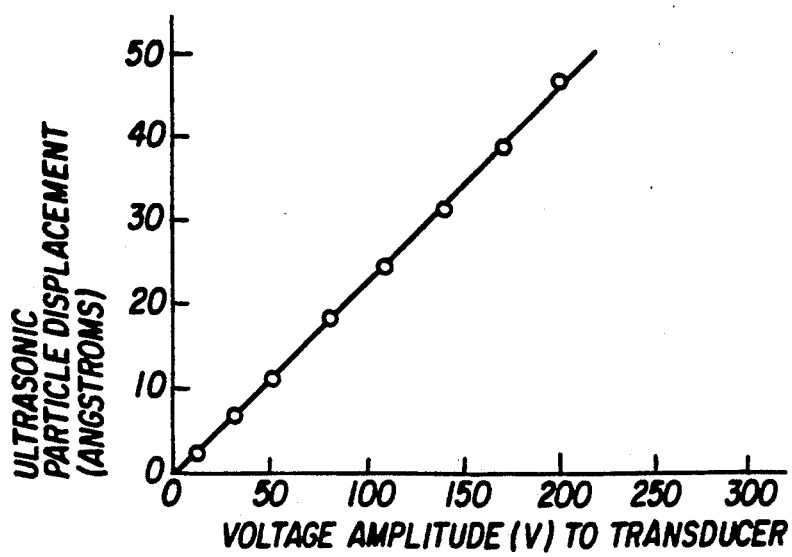
FIG. 6 is a plot showing the relationship of the ESAT output signal resulting from the time-varying capacitance change of the membrane and movement of the membrane relative to the central electrode.

On the Fast Fourier Transform plot, assume that there is a 1 volt signal amplitude corresponding to a frequency of 1 MHz. Using the 1.5 ratio, the Fast Fourier Transform plot is normalized so that a 1.5 volt signal corresponds to 1 MHz. FIG. 6 shows that the ESAT voltage output is directly proportional to the amplitude of the sinusoidal movement (in angstroms) of the membrane 18 relative to the central electrode 23 at a given frequency. Therefore, the movement of the membrane is determined at 1 MHz.

In step 314, characteristics of the membrane are eliminated from the normalized Fast Fourier Transform plot. The membrane characteristics are determined by the following equation:

$$|\eta_0| = \frac{2|\xi_0|}{\sqrt{1 + (\sigma\omega/\rho V_1)^2}} \qquad (2)$$

where
$\sigma$ is the areal density of the membrane;
$\omega$ is the angular frequency;

$\rho$ is the mass density of the liquid;
$V_L$ is the speed of the ultrasonic wave in the liquid;
$|\eta_o|$ is the modulus of the sinusoidal movement (displacement) of the membrane; and
$|\xi_o|$ is the modulus of the ultrasonic wave displacement amplitude.

The derivation of the above equation along with other calibration information are completely described in *Absolute Ultrasonic Displacement Amplitude Measurements with a Submersible Electrostatic Acoustic Transducer*, William T. Yost and John H. Cantrell (*Review of Scientific Instruments*, Volume 63, No. 9, September 1992)., which is incorporated in its entirety herein by reference. The membrane characteristics usually affect the plot in the higher frequency ranges. An attenuation at higher frequencies (a tilt on one side of the plot) is usually corrected after the membrane characteristics are eliminated.

The membrane effect depends on the frequency at which the measurement of the ESAT output signal is made. For example, a typical membrane has a 3 dB point (that frequency where $\sigma\omega=\rho V_L$ for the membrane-water coupling) at a frequency of 2.43 MHz. The uncertainty contribution for the membrane is approximately 1.3%. The limit of the uncertainty for this membrane is 1.6% and the total measurement uncertainty is thus between 2.3% to 3.9%.

After correcting for the membrane, the higher portion of the Fast Fourier Transform plot is adjusted to eliminate the membrane effect. For instance, at 15 MHz there may be 6 dB difference between the actual signal and what the signal should be. The adjustment is made so that the membrane is correctly represented by the Fast Fourier Transform plot.

In step 316, the transfer function for the UT 102 is determined using the final normalized Fast Fourier Transform plot and the absolute calibration of the toneburst. Using this transfer function, the parameters of the wave motion can be determined. Examples of these parameters are the energy and the energy density of the wave. The amplitude of the soundwave and determination of certain liquid properties can be made.

A second preferred embodiment also measures the amplitude of vibration of membrane 18. The UT 102, which is connected to the pulsed oscillator 106, generates a wave as before. The ESAT 10 is configured to give a frequency modulated output about some central frequency (FM signal). The operational circuitry selects the specific frequency (sideband) of FM signal and analyzes the amplitude of that frequency in steps 302 through 306 of the first preferred embodiment.

A third preferred embodiment performs an absolute calibration for each frequency to calibrate the UT 102 under test. The equipment set-up is the same as used in the first preferred embodiment and shown in FIG. 2. The UT 102 is submerged in a liquid and generates ultrasonic waves at a specific frequency, e.g. tonebursts. The change capacitance in the ESAT 10 due to the ultrasonic waves is measured. The membrane characteristics (see equation (2) above) and diffraction effects are eliminated and the result is plotted. After all of the applicable frequencies have been generated by the UT and the output signal from the ESAT are plotted, a transfer function for the UT 102 can be determined.

The number of frequencies measured depends on the accuracy of the plotted graph needed and the frequency region of interest. For example, if 1 MHz is the desired frequency of operation of the UT, then 10 tonebursts ranging from 950 Hz to 1.05 MHz may be used to create the plot.

Although the invention has been described and illustrated with particularity, it is intended to be illustrative of preferred embodiments. It is understood that the disclosure has been made by way of example only. Numerous changes in the combination and arrangements of the parts, steps, and features can be made by those skilled in the art without departing from the spirit and scope of the invention, as hereinafter claimed.

What is claimed is:

1. A method of standardizing a transducer under test by using an electrostatic acoustic transducer comprising the steps of:

measuring a first output signal resulting from movement of the membrane of the electrostatic acoustic transducer caused by a first waveform generated by the transducer under test, the first waveform having a single frequency;

monitoring a second output signal of the electrostatic acoustic transducer while applying a second waveform having a plurality of frequencies generated by the transducer under test;

generating a plot based on the monitored second output signal of the electrostatic acoustic transducer, the plot utilizing a Fast Fourier Transform procedure;

normalizing the plot based on the first output signal of the electrostatic acoustic transducer;

modifying the plot to correct for membrane characteristics of the electrostatic acoustic transducer; and determining a transfer function based on the modified plot for representing characteristics of the transducer under test.

2. The method of claim 1, wherein the first and second output signals are a capacitive generated voltage between an electrode and the membrane of the electrostatic acoustic transducer.

3. The method of claim 1, wherein the first output signal is a frequency modulated signal generated from a capacitive generated voltage between an electrode and the membrane of the electrostatic acoustic transducer.

4. The method of claim 1, wherein a toneburst is used to generate the first waveform.

5. The method of claim 1, wherein the second waveform is generated by a voltage spike.

6. The method of claim 5, wherein the voltage spike contains all the appropriate frequencies.

7. The method of claim 1, wherein membrane characteristics are based on the following equation:

$$|\eta_0| = \frac{2|\xi_0|}{\sqrt{1 + (\sigma\omega/\rho V_1)^2}}$$

where
$\sigma$ is the areal density of the membrane;
$\omega$ is the angular frequency;
$\rho$ is the mass density of the liquid;
$V_L$ is the speed of the ultrasonic wave in the liquid;
$|\eta_o|$ is the membrane displacement amplitude; and
$|\xi_o|$ is the ultrasonic particle displacement amplitude.

8. The method of claim 1, wherein the step of modifying the plot also corrects for diffraction effects.

9. The method of claim 1, wherein the transfer function represents the output signals of the electrostatic acoustic transducer as a function of frequency.

10. The method of claim 1, wherein the step of normalizing the plot uses the Fast Fourier Transform of the first output signal.

11. The method of claim 1, wherein an absolute calibration of the single frequency is performed by matching the first output signal of the electrostatic acoustic transducer with the output of a calibration generator.

12. The method of claim 11, wherein the step of determining the transfer function uses the absolute calibration of the single frequency.

13. A method of standardizing a transducer under test by using an electrostatic acoustic transducer having a membrane, the transducer under test being connected to a waveform generator and being submerged in a liquid containing the electrostatic acoustic transducer, the method comprising the steps of:
generating a first waveform having a single frequency by outputting a pulse from the waveform generator to the transducer under test;
measuring a first output signal from the electrostatic acoustic transducer resulting from movement of the membrane caused by the first waveform;
generating a second waveform having a plurality of frequencies by outputting a voltage spike from the waveform generator to the transducer under test;
monitoring a second output signal from the electrostatic acoustic transducer resulting from the movement of the membrane caused by the second waveform;
generating a plot based on the second output signal by utilizing a Fast Fourier Transform procedure;
normalizing the plot based on the first output signal;
modifying the plot to correct for membrane characteristics; and
determining a transfer function based on the modified plot for representing characteristics of the transducer under test.

14. The method of claim 13, wherein the first and second output signals are a capacitive generated voltage between an electrode and the membrane of the electrostatic acoustic transducer.

15. The method of claim 13, wherein the first output signal is a frequency modulated signal generated from a capacitive generated voltage between an electrode and the membrane of the electrostatic acoustic transducer.

16. The method of claim 13, wherein a toneburst is used to generate the first waveform.

17. The method of claim 13, wherein the second waveform is generated by a voltage spike and contains substantially all frequencies measurable by the electrostatic acoustic transducer.

18. The method of claim 17, wherein the voltage spike contains all the appropriate frequencies.

19. The method of claim 13, wherein membrane characteristics are based on the following equation:

$$|\eta_0| = \frac{2|\xi_0|}{\sqrt{1 + (\sigma\omega/\rho V_1)^2}}$$

where
$\sigma$ is the areal density of the membrane;
$\omega$ is the angular frequency;
$\rho$ is the mass density of the liquid;
$V_L$ is the speed of the ultrasonic wave in the liquid;
$|\eta_o|$ is the membrane displacement amplitude; and
$|\xi_o|$ is the ultrasonic particle displacement amplitude.

20. The method of claim 13, wherein the step of modifying the plot also corrects for diffraction effects.

21. The method of claim 13, wherein the transfer function represents the output signals of the electrostatic acoustic transducer as a function of frequency.

22. The method of claim 13, wherein the step of normalizing the plot uses the Fast Fourier Transform of the first output signal.

23. The method of claim 13, wherein an absolute calibration of the pulse is performed by matching the first output signal of the electrostatic acoustic transducer with the output of a calibration generator.

24. The method of claim 23, wherein the step of determining the transfer function uses the absolute calibration of the pulse.

25. The method of claim 8, wherein the electrostatic acoustic transducer is axially aligned with the transducer under test.

26. A method of standardizing a transducer under test by using an electrostatic acoustic transducer having a membrane, the transducer under test being connected to a waveform generator and being submerged in a liquid containing the electrostatic acoustic transducer, the method comprising the steps of:
generating a plurality of waveforms by outputting a plurality of pulses from the waveform generator to the transducer under test, each waveform having a single frequency;
measuring output signals from the electrostatic acoustic transducer resulting from movement of the membrane caused by each waveform;
modifying the output signals to correct for membrane characteristics;
generating a plot based on the modified output signals; and
determining a transfer function based on the plot for representing characteristics of the transducer under test.

27. The method of claim 26, wherein the output signals are a capacitive generated voltage between an electrode and the membrane of the electrostatic acoustic transducer.

28. The method of claim 26, wherein the output signals are a frequency modulated signal generated from a capacitive generated voltage between an electrode and the membrane of the electrostatic acoustic transducer.

29. The method of claim 26, wherein a toneburst is used to generate each waveform.

30. The method of claim 26, wherein membrane characteristics are based on the following equation:

$$|\eta_0| = \frac{2|\xi_0|}{\sqrt{1 + (\sigma\omega/\rho V_1)^2}}$$

where
$\sigma$ is the areal density of the membrane;
$\omega$ is the angular frequency;
$\rho$ is the mass density of the liquid;
$V_L$ is the speed of the ultrasonic wave in the liquid;
$|\eta_o|$ is the membrane displacement amplitude; and
$|\xi_o|$ is the ultrasonic particle displacement amplitude.

31. The method of claim 26, wherein the step of modifying the output signals also corrects for diffraction effects.

* * * * *